US009913710B2

United States Patent
Perriello et al.

(10) Patent No.: US 9,913,710 B2
(45) Date of Patent: Mar. 13, 2018

(54) IMPLANTABLE BIOLOGIC HOLDER (71) Applicant: SMITH & NEPHEW, INC., Memphis, TN (US)

(72) Inventors: Michael James Perriello, Hopedale, MA (US); Alfred Rodrigue Berube, Jr., North Attleboro, MA (US); Steven Mark Bowman, Sherborn, MA (US); John Albert Slusarz, Jr., Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/935,557

(22) Filed: Nov. 9, 2015

(65) Prior Publication Data
US 2016/0058550 A1 Mar. 3, 2016

Related U.S. Application Data (62) Division of application No. 13/365,000, filed on Feb. 2, 2012, now Pat. No. 9,204,959.

(51) Int. Cl.
*A61F 2/08* (2006.01)

(52) U.S. Cl.
CPC ..... *A61F 2/0811* (2013.01); *A61F 2002/0829* (2013.01); *A61F 2002/0852* (2013.01); *A61F 2002/0882* (2013.01); *A61F 2250/0068* (2013.01)

(58) Field of Classification Search
CPC .. A61F 2/3603; A61F 2/30756; A61F 2/3872; A61F 2/4618; A61B 5/4514

USPC .......................................... 623/14.12, 17.11
See application file for complete search history.

(56) References Cited

U.S. PATENT DOCUMENTS

| 3,176,316 | A |   | 4/1965  | Bodell         |            |
|-----------|---|---|---------|----------------|------------|
| 3,613,120 | A |   | 10/1971 | McFarland, Jr. |            |
| 4,255,820 | A |   | 3/1981  | Rothermel et al. |          |
| 4,344,193 | A | * | 8/1982  | Kenny ........... | A61F 2/3872 |
|           |   |   |         |                | 128/DIG. 21 |

(Continued)

FOREIGN PATENT DOCUMENTS

| EP | 1108401 A1   | 6/2001  |
|----|--------------|---------|
| JP | H11318959 A  | 11/1999 |

(Continued)

OTHER PUBLICATIONS

Communication from European Patent Office from related European Application No. 13703711.5-1666 dated Aug. 9, 2016.

(Continued)

*Primary Examiner* — Alvin Stewart
(74) *Attorney, Agent, or Firm* — Burns & Levinson, LLP; Joseph M. Maraia (57) ABSTRACT

A tissue graft suspension device includes a platform member, a graft connecting element coupled to the platform member such that a portion of the graft connecting element forms a loop for attachment to a tissue graft, and an enclosure member coupled to the loop of the graft connecting element and configured to enclose a biologic material. The enclosure member defines an opening configured to receive the biologic material. The graft connecting element and the enclosure member are configured such that, during use, the tissue graft is coupled to the loop and in contact with the enclosure member.

19 Claims, 8 Drawing Sheets

(56) References Cited

U.S. PATENT DOCUMENTS

| | | | |
|---|---|---|---|
| 4,469,101 A | 9/1984 | Coleman et al. | |
| 4,502,161 A * | 3/1985 | Wall | A61F 2/30756 |
| | | | 606/286 |
| 4,584,722 A | 4/1986 | Levy et al. | |
| 4,642,119 A | 2/1987 | Shah | |
| 4,662,886 A | 5/1987 | Moorse et al. | |
| 4,731,084 A | 3/1988 | Dunn et al. | |
| 4,744,793 A | 5/1988 | Parr et al. | |
| 4,773,910 A | 9/1988 | Chen et al. | |
| 4,834,755 A | 5/1989 | Silvestrini et al. | |
| 4,863,471 A | 9/1989 | Mansat | |
| 4,917,699 A | 4/1990 | Chervitz | |
| 4,917,700 A | 4/1990 | Aikins | |
| 4,919,667 A * | 4/1990 | Richmond | A61F 2/3872 |
| | | | 623/14.12 |
| 5,041,118 A | 8/1991 | Wasilewski | |
| 5,067,964 A * | 11/1991 | Richmond | A61F 2/30756 |
| | | | 623/14.12 |
| 5,092,894 A * | 3/1992 | Kenny | A61F 2/3872 |
| | | | 128/898 |
| 5,158,574 A * | 10/1992 | Stone | A61F 2/08 |
| | | | 264/108 |
| 5,171,322 A * | 12/1992 | Kenny | A61F 2/3872 |
| | | | 623/14.12 |
| 5,176,708 A | 1/1993 | Frey et al. | |
| 5,269,783 A * | 12/1993 | Sander | A61B 17/06 |
| | | | 606/148 |
| 5,306,301 A | 4/1994 | Graf et al. | |
| 5,456,721 A * | 10/1995 | Legrand | A61F 2/0805 |
| | | | 623/1.5 |
| 5,507,812 A | 4/1996 | Moore | |
| 5,549,676 A | 8/1996 | Johnson | |
| 5,632,745 A * | 5/1997 | Schwartz | A61B 17/1604 |
| | | | 606/104 |
| 5,645,588 A | 7/1997 | Graf et al. | |
| 5,711,960 A * | 1/1998 | Shikinami | A61F 2/0063 |
| | | | 424/425 |
| 5,769,894 A | 6/1998 | Ferragamo | |
| 6,027,744 A | 2/2000 | Vacanti et al. | |
| 6,056,752 A | 5/2000 | Roger | |
| 6,103,255 A * | 8/2000 | Levene | A61L 27/3839 |
| | | | 424/426 |
| 6,143,029 A | 11/2000 | Rippstein | |
| 6,193,754 B1 | 2/2001 | Seedhom | |
| 6,203,572 B1 | 3/2001 | Johnson et al. | |
| 6,214,047 B1 | 4/2001 | Melvin | |
| 6,245,107 B1 * | 6/2001 | Ferree | A61B 17/025 |
| | | | 606/279 |
| 6,267,767 B1 | 7/2001 | Strobel et al. | |
| 6,280,474 B1 | 8/2001 | Cassidy et al. | |
| 6,283,996 B1 | 9/2001 | Chervitz et al. | |
| 6,296,659 B1 | 10/2001 | Foerster | |
| 6,325,804 B1 | 12/2001 | Wenstrom, Jr. et al. | |
| 6,371,990 B1 * | 4/2002 | Ferree | A61F 2/441 |
| | | | 623/17.16 |
| 6,428,576 B1 * | 8/2002 | Haldimann | A61F 2/442 |
| | | | 623/17.16 |
| 6,508,839 B1 * | 1/2003 | Lambrecht | A61F 2/442 |
| | | | 128/898 |
| 6,517,542 B1 | 2/2003 | Byerman | |
| 6,517,578 B2 | 2/2003 | Hein | |
| 6,554,862 B2 | 4/2003 | Overaker | |
| 6,579,291 B1 * | 6/2003 | Keith | A61B 17/70 |
| | | | 128/898 |
| 6,599,319 B2 | 7/2003 | Knudsen et al. | |
| 6,602,290 B2 | 8/2003 | Esnouf et al. | |
| 6,602,291 B1 * | 8/2003 | Ray | A61F 2/441 |
| | | | 623/16.11 |
| 6,620,185 B1 * | 9/2003 | Harvie | A61B 17/0401 |
| | | | 606/215 |
| 6,638,309 B2 | 10/2003 | Bonutti | |
| 6,669,707 B1 * | 12/2003 | Swanstrom | A61B 17/0643 |
| | | | 606/151 |
| 6,736,815 B2 * | 5/2004 | Ginn | A61F 2/4611 |
| | | | 606/246 |
| 6,752,831 B2 | 6/2004 | Sybert et al. | |
| 6,767,037 B2 * | 7/2004 | Wenstrom, Jr. | A61B 17/0401 |
| | | | 289/1.2 |
| 6,843,799 B2 * | 1/2005 | Bartlett | A61B 17/0401 |
| | | | 606/232 |
| 6,866,681 B2 | 3/2005 | Laboureau et al. | |
| 6,872,227 B2 | 3/2005 | Sump et al. | |
| 6,964,674 B1 * | 11/2005 | Matsuura | A61B 17/0057 |
| | | | 606/213 |
| 6,972,027 B2 * | 12/2005 | Fallin | A61B 17/0401 |
| | | | 606/139 |
| 7,001,390 B2 | 2/2006 | Gebhardt et al. | |
| 7,004,970 B2 * | 2/2006 | Cauthen, III | A61F 2/441 |
| | | | 128/898 |
| 7,033,393 B2 * | 4/2006 | Gainor | A61B 17/0401 |
| | | | 606/213 |
| 7,097,654 B1 | 8/2006 | Freedland | |
| 7,198,047 B2 * | 4/2007 | Lambrecht | A61B 17/70 |
| | | | 128/898 |
| 7,273,497 B2 * | 9/2007 | Ferree | A61F 2/2846 |
| | | | 623/17.16 |
| 7,309,356 B2 | 12/2007 | Steiner | |
| 7,445,634 B2 * | 11/2008 | Trieu | A61F 2/442 |
| | | | 606/232 |
| 7,594,922 B1 * | 9/2009 | Goble | A61B 17/0483 |
| | | | 606/213 |
| 7,601,155 B2 | 10/2009 | Petersen | |
| 7,717,961 B2 * | 5/2010 | Lambrecht | A61B 5/1076 |
| | | | 606/99 |
| 7,850,711 B1 | 12/2010 | Stone et al. | |
| 7,857,857 B2 * | 12/2010 | Kim | A61F 2/442 |
| | | | 623/17.11 |
| 7,896,917 B2 | 3/2011 | Walters et al. | |
| 7,901,455 B2 | 3/2011 | Koob et al. | |
| 7,901,461 B2 * | 3/2011 | Harmon | A61L 27/3683 |
| | | | 623/23.72 |
| 7,905,918 B2 | 3/2011 | Cimino | |
| 7,914,553 B2 * | 3/2011 | Ferree | A61B 17/1671 |
| | | | 606/232 |
| 7,988,732 B2 | 8/2011 | Bojarski et al. | |
| 8,097,033 B2 | 1/2012 | Tse | |
| 8,137,400 B2 | 3/2012 | Shino | |
| 8,162,997 B2 | 4/2012 | Struhl | |
| 8,177,839 B2 | 5/2012 | Koob et al. | |
| 8,202,306 B2 | 6/2012 | Dreyfuss | |
| 8,226,715 B2 | 7/2012 | Hwang et al. | |
| 8,231,678 B2 * | 7/2012 | Lambrecht | A61F 2/4611 |
| | | | 623/17.11 |
| 8,357,203 B2 * | 1/2013 | White | A61B 17/562 |
| | | | 623/14.12 |
| 8,439,976 B2 | 5/2013 | Albertorio et al. | |
| 8,449,561 B2 * | 5/2013 | Bowman | A61B 17/0642 |
| | | | 606/151 |
| 8,460,350 B2 | 6/2013 | Albertorio et al. | |
| 8,486,143 B2 | 7/2013 | Laurencin et al. | |
| 8,545,558 B2 | 10/2013 | Spenciner et al. | |
| 8,597,311 B2 | 12/2013 | Criscuolo et al. | |
| 8,597,352 B2 * | 12/2013 | Schwartz | A61F 2/0811 |
| | | | 623/14.12 |
| 8,663,324 B2 | 3/2014 | Schmieding et al. | |
| 8,801,790 B2 * | 8/2014 | Trieu | A61F 2/441 |
| | | | 623/17.12 |
| 9,204,959 B2 * | 12/2015 | Perriello | A61F 2/0811 |
| 2001/0041916 A1 * | 11/2001 | Bonutti | A61B 17/0401 |
| | | | 606/232 |
| 2002/0019670 A1 | 2/2002 | Crawley et al. | |
| 2002/0055749 A1 | 5/2002 | Esnouf et al. | |
| 2002/0072797 A1 | 6/2002 | Hays et al. | |
| 2002/0147461 A1 * | 10/2002 | Aldrich | A61F 2/442 |
| | | | 606/213 |
| 2002/0151979 A1 * | 10/2002 | Lambrecht | A61B 17/70 |
| | | | 623/17.16 |
| 2002/0156476 A1 | 10/2002 | Wilford | |
| 2002/0161439 A1 | 10/2002 | Strobel et al. | |
| 2003/0023304 A1 | 1/2003 | Carter et al. | |

(56) References Cited

U.S. PATENT DOCUMENTS

| | | | |
|---|---|---|---|
| 2003/0036797 A1* | 2/2003 | Malaviya | A61B 17/064 623/14.12 |
| 2003/0040796 A1* | 2/2003 | Ferree | A61B 17/1671 623/17.11 |
| 2003/0065361 A1 | 4/2003 | Dreyfuss | |
| 2003/0078579 A1* | 4/2003 | Ferree | A61F 2/441 606/53 |
| 2003/0153976 A1* | 8/2003 | Cauthen, III | A61F 2/441 623/17.16 |
| 2003/0187445 A1* | 10/2003 | Keith | A61B 17/0401 623/17.11 |
| 2003/0195514 A1* | 10/2003 | Trieu | A61F 2/442 623/17.11 |
| 2003/0212456 A1* | 11/2003 | Lipchitz | A61F 2/08 623/13.17 |
| 2004/0002764 A1* | 1/2004 | Gainor | A61B 17/0401 623/17.16 |
| 2004/0039392 A1* | 2/2004 | Trieu | A61F 2/442 606/86 R |
| 2004/0059416 A1* | 3/2004 | Murray | A61L 24/043 623/13.15 |
| 2004/0097980 A1* | 5/2004 | Ferree | A61F 2/2846 606/151 |
| 2004/0138703 A1* | 7/2004 | Alleyne | A61F 2/442 606/213 |
| 2004/0153153 A1 | 8/2004 | Elson et al. | |
| 2004/0267362 A1 | 12/2004 | Hwang et al. | |
| 2005/0004670 A1 | 1/2005 | Gebhardt et al. | |
| 2005/0033363 A1* | 2/2005 | Bojarski | A61B 17/0401 606/228 |
| 2005/0070906 A1 | 3/2005 | Clark et al. | |
| 2005/0125077 A1* | 6/2005 | Harmon | A61L 27/3683 623/23.72 |
| 2005/0177240 A1* | 8/2005 | Blain | A61F 2/442 623/17.15 |
| 2005/0234463 A1 | 10/2005 | Parcher | |
| 2005/0283246 A1* | 12/2005 | Cauthen, III | A61B 17/0057 623/17.16 |
| 2006/0190041 A1 | 8/2006 | Fallin et al. | |
| 2006/0241756 A1* | 10/2006 | Fritz | C12N 5/0655 623/14.12 |
| 2006/0247776 A1* | 11/2006 | Kim | A61F 2/442 623/17.12 |
| 2007/0005069 A1 | 1/2007 | Contiliano | |
| 2007/0005140 A1* | 1/2007 | Kim | A61B 17/7095 623/17.16 |
| 2007/0049944 A1 | 3/2007 | Stone et al. | |
| 2007/0067040 A1* | 3/2007 | Ferree | A61F 2/442 623/17.16 |
| 2007/0073394 A1* | 3/2007 | Seedhom | A61F 2/30756 623/14.12 |
| 2007/0093896 A1* | 4/2007 | Malinin | A61B 17/1604 623/14.12 |
| 2007/0100348 A1* | 5/2007 | Cauthen, III | A61B 17/0401 606/99 |
| 2007/0100450 A1* | 5/2007 | Hodorek | A61F 2/30721 623/14.12 |
| 2007/0118218 A1* | 5/2007 | Hooper | A61B 17/562 623/14.12 |
| 2007/0179607 A1* | 8/2007 | Hodorek | A61F 2/30749 623/14.12 |
| 2007/0198021 A1* | 8/2007 | Wales | A61B 17/0057 606/86 R |
| 2007/0225805 A1 | 9/2007 | Schmieding | |
| 2008/0046009 A1 | 2/2008 | Albertorio et al. | |
| 2008/0097606 A1* | 4/2008 | Cragg | A61F 2/3872 623/14.12 |
| 2008/0188933 A1 | 8/2008 | Koob et al. | |
| 2008/0195205 A1* | 8/2008 | Schwartz | A61B 17/0642 623/14.12 |
| 2008/0234819 A1 | 9/2008 | Schmieding et al. | |
| 2008/0255665 A1* | 10/2008 | Weissberg | A61F 2/08 623/14.12 |
| 2008/0269895 A1* | 10/2008 | Steinwachs | A61L 27/3612 623/14.12 |
| 2008/0319546 A1 | 12/2008 | Bojarski et al. | |
| 2009/0043342 A1 | 2/2009 | Freedland | |
| 2009/0060974 A1 | 3/2009 | Schmieding et al. | |
| 2009/0138015 A1* | 5/2009 | Conner | A61B 17/1615 606/80 |
| 2009/0157184 A1* | 6/2009 | Cauthen, III | A61B 17/0057 623/17.11 |
| 2009/0164014 A1* | 6/2009 | Liljensten | A61F 2/30756 623/16.11 |
| 2009/0171467 A1* | 7/2009 | Mann | A61F 2/30756 623/23.63 |
| 2009/0214613 A1 | 8/2009 | Lasso Vzquez et al. | |
| 2009/0234387 A1 | 9/2009 | Quinones | |
| 2009/0259311 A1* | 10/2009 | Shterling | A61F 2/30965 623/14.12 |
| 2009/0292315 A1* | 11/2009 | Trieu | A61B 17/7065 606/249 |
| 2009/0306776 A1 | 12/2009 | Murray | |
| 2010/0040662 A1 | 2/2010 | Cotton et al. | |
| 2010/0125297 A1 | 5/2010 | Guederian et al. | |
| 2010/0249930 A1 | 9/2010 | Myers | |
| 2010/0324676 A1 | 12/2010 | Albertorio et al. | |
| 2011/0093073 A1* | 4/2011 | Gatt | A61F 2/30756 623/14.12 |
| 2012/0095470 A1 | 4/2012 | Stone | |
| 2012/0109302 A1* | 5/2012 | Miller | A61F 2/4455 623/17.11 |
| 2012/0191187 A1* | 7/2012 | Tallarida | A61B 17/8615 623/14.12 |
| 2013/0060334 A1* | 3/2013 | Kurzweil | A61L 27/18 623/14.12 |
| 2013/0079877 A1* | 3/2013 | Buma | A61F 2/3872 623/14.12 |
| 2013/0172999 A1* | 7/2013 | Kaplan | A61L 27/3604 623/14.12 |
| 2013/0312897 A1* | 11/2013 | Vowles | A61B 17/0401 156/83 |
| 2013/0345810 A1 | 12/2013 | Jaeger et al. | |
| 2014/0025166 A1 | 1/2014 | Bonutti | |
| 2014/0222149 A1* | 8/2014 | Amis | A61F 2/3872 623/14.12 |
| 2014/0277451 A1* | 9/2014 | Ganz | A61F 2/3872 623/14.12 |
| 2015/0238318 A1* | 8/2015 | McCullen | A61F 2/30756 623/14.12 |

FOREIGN PATENT DOCUMENTS

| | | |
|---|---|---|
| JP | 2000210311 A | 8/2000 |
| JP | 2002-35018 A | 2/2002 |
| JP | 2005305162 A | 11/2005 |
| JP | 2009153710 A | 7/2009 |
| WO | WO 92/16167 A1 | 10/1992 |
| WO | 01/15634 A1 | 3/2001 |
| WO | WO 2008/048578 A1 | 4/2008 |
| WO | 2008082588 A2 | 7/2008 |
| WO | 2010121302 A1 | 10/2010 |
| WO | 2012056384 A2 | 5/2012 |

OTHER PUBLICATIONS

First Office Action from related Chinese Application No. 201380018374 dated Oct. 27, 2015.

International Search Report, PCT/US2013/024235, dated Jul. 18, 2013, pp. 8.

Second Office Action from related Chinese Application No. 201380018374.X dated Jun. 6, 2016.

Office Action from related Japanese Application No. 2014-555728 dated Sep. 26, 2016.

Third Office Action from related Chinese Application No. 201380018374.X dated Sep. 18, 2016.

(56) References Cited

OTHER PUBLICATIONS

Office Action in Corresponding Russian Application No. 2014133464/14(053988) dated Jan. 9, 2017.
Notice of Reasons for Rejection from related Japanese Application No. 2014-555727 dated Jun. 26, 2016.
Office Action from related Russian Application No. 2014133464/14(053988) dated Apr. 27, 2017.
Examination Report from related Australian Application No. 2013215000 dated Jun. 6, 2017.
CN Office Action for CN App No. 201280023011.0 dated Jul. 18, 2017, 3 pages.

* cited by examiner

IMPLANTABLE BIOLOGIC HOLDER

CROSS REFERENCE TO RELATED APPLICATION

This application is a divisional application and claims benefit of and priority to the co-pending U.S. application Ser. No. 13/365,000, filed Feb. 2, 2012, the entire content of which is incorporated by reference herein.

TECHNICAL FIELD

This document relates to an implantable biologic holder.

BACKGROUND

A ligament, such as an anterior cruciate ligament (ACL), that has ruptured and is non-repairable may be replaced arthroscopically by a tissue graft. The tissue graft can be natural and harvested from another part of the body. For example, in the case of an ACL repair, the tissue graft can be harvested from a portion of a patellar tendon having so called "bone blocks" at each end, and from the semitendonosis and gracilis. Alternatively, the tissue graft can be formed from synthetic materials or from a combination of synthetic and natural materials. When repairing an ACL, the replacement tissue graft can be implanted by securing one end of the tissue graft in a socket formed in a passage within the femur, and passing the other end of the graft through a passage formed in the tibia.

A biologic material, such as a fibrin clot, can be inserted into a ligament or other soft tissue injury site, for example via a cannula, or attached directly to a tissue graft, for example by suturing, to promote healing. The application of a biologic material to an injury site can help promote healing.

SUMMARY

According to one aspect, a tissue graft suspension device includes a platform member, a graft connecting element coupled to the platform member such that a portion of the graft connecting element forms a loop for attachment to a tissue graft, and an enclosure member coupled to the loop of the graft connecting element and configured to enclose a biologic material. The enclosure member defines an opening configured to receive the biologic material. The graft connecting element and the enclosure member are configured such that, during use, the tissue graft is coupled to the loop and in contact with the enclosure member.

Implementations of this aspect may include one or more of the following features.

For example, the graft connecting element may be a continuous loop of suture. The loop may pass through the opening of the enclosure member. The loop may pass through an attachment element of the enclosure member. The enclosure member may define two openings configured to receive the biologic material. The biologic material may be a fibrin clot. The biologic material may be a platelet rich plasma. The tissue graft suspension device may further include one or more filaments attached to the enclosure member.

According to another aspect, a method of securing a tissue graft includes providing a platform member coupled to a graft connecting element, the graft connecting element being coupled to an enclosure member and forming a loop for attachment to the tissue graft, the enclosure member configured to enclose a biologic material, inserting the biologic material through an opening in the enclosure member, attaching the tissue graft to the graft connecting element such that the tissue graft is in contact with the enclosure member, forming a bone tunnel in a bone, and positioning the platform member on a surface of the bone such that at least a portion of the tissue graft is in the bone tunnel.

Implementations of this aspect may include one or more of the following features.

For example, attaching the tissue graft to the graft connecting element may include looping the tissue graft through the loop of the graft connecting element such that the enclosure member is positioned between two portions of the tissue graft. Attaching the tissue graft to the graft connecting element may include looping the graft connecting element through an opening in a bone block of the tissue graft. The bone tunnel may include a first opening and a second opening. Positioning the platform member on the surface of the bone may include inserting the platform member into the bone tunnel through the first opening and into the bone tunnel, moving the platform member through the tunnel and out the second opening, and positioning the platform member over the second opening with the graft connecting element extending into the bone tunnel such that a first portion of the tissue graft attached to the graft connecting element is in the tunnel and a second portion of the tissue graft extends out of the first opening.

According to yet another aspect, a scaffold for receiving a biologic material includes a central portion impregnated with a biologic material, the central portion comprising filaments arranged in a weave pattern, and a guide portion attached to an edge of the central portion, the guide portion comprising one or more filaments. The scaffold is configured to be inserted into a tear in soft tissue.

Implementations of this aspect may include one or more of the following features.

For example, the tear in soft tissue may be a meniscal tear. The guide portion may include a first guide portion attached to a first edge of the central portion, and a second guide portion attached to a second edge of the central portion, the second edge being opposite the first edge. The guide portion may include one or more filaments extending out from the weave pattern of the central portion.

According to a further aspect, a method of repairing a soft tissue tear includes providing a scaffold comprising a central portion and a guide portion, the central portion comprising filaments arranged in a weave pattern, impregnating the central portion of the scaffold with a biologic material, inserting an edge of the scaffold into the soft tissue tear, and moving the central portion of the scaffold within the soft tissue tear into a final position by manipulating the guide portion.

Implementations of this aspect may include one or more of the following features.

For example, the soft tissue may be a meniscus. Impregnating the central portion of the scaffold with a biologic material may include forming at least one of a fibrin clot or a platelet rich plasma around the central portion. Impregnating the central portion of the scaffold may include pressing the central portion into at least one of a fibrin clot or a platelet rich plasma.

The details of one or more implementations are set forth in the accompanying drawings and the description below. Other features, aspects, and advantages will become apparent from the description, the drawings, and the claims.

DETAILED DESCRIPTION

This document describes examples of an implantable enclosure member and an implantable scaffold that can hold a biologic material, for example a fibrin clot, and be positioned within a ligament or other soft tissue repair site such that the biologic material comes in contact with the ligament or other soft tissue.

Figure 1A:
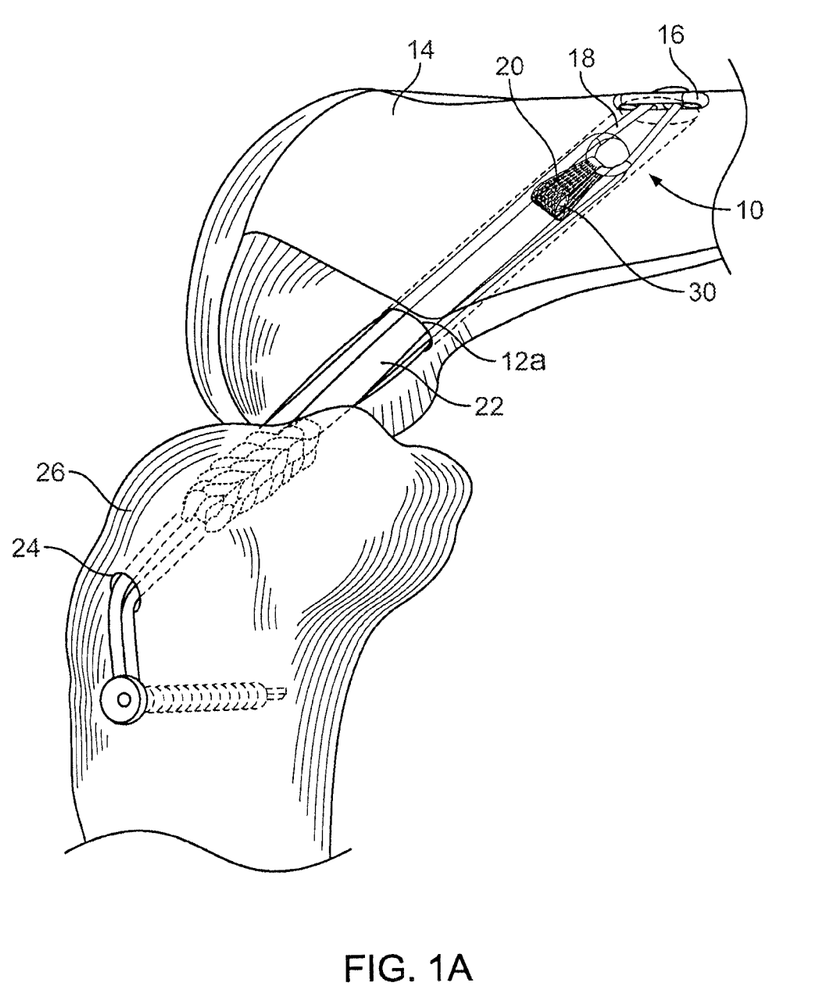
FIG. 1A is a perspective view of a graft attachment device implanted within a femur.
Figure 1B:
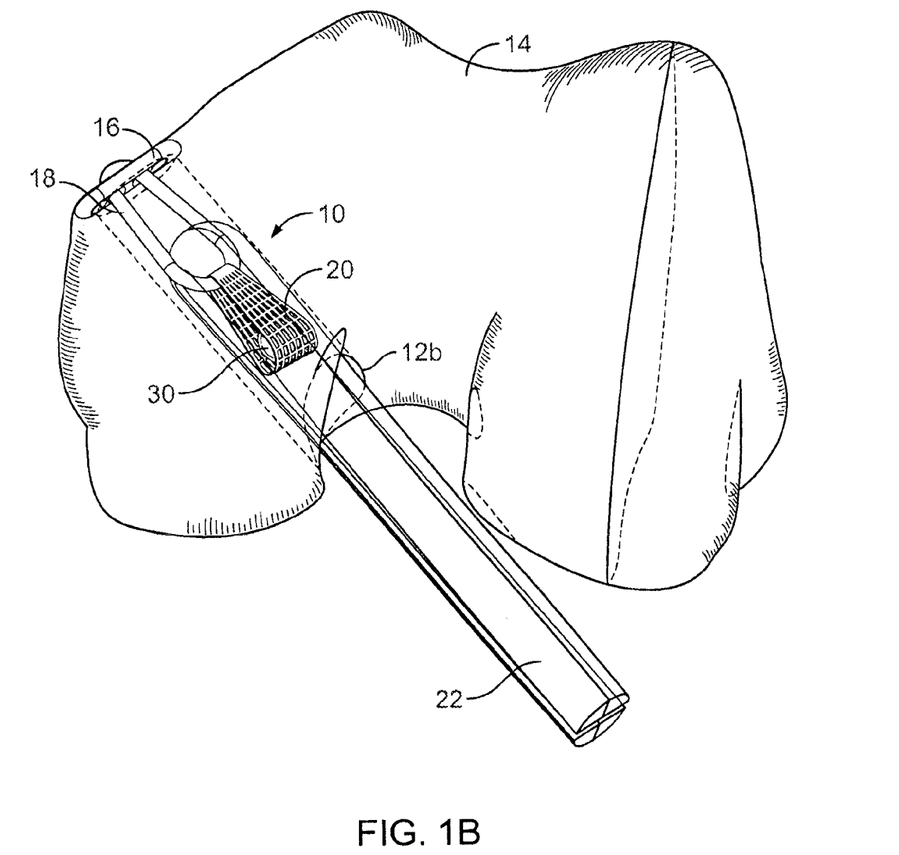
FIG. 1B is a perspective view of an alternative implantation of the graft attachment device within the femur.

Referring to FIG. 1A, a graft attachment device 10 is implanted during, for example, an anterior cruciate ligament (ACL) repair and reconstruction procedure, and is positioned within a femoral tunnel 12a of a femur 14. In some cases, the graft attachment device 10 can be positioned within a shorter femoral tunnel 12b (FIG. 1B). The graft attachment device 10 includes a platform member 16, a graft connecting element 18, and an enclosure member 20, and can be coupled to a tissue graft 22, for example a semitendonosis and gracilis graft. The femoral tunnel 12a, 12b can receive one end of the graft 22 while a tibial tunnel 24 located within a tibia 26 can receive the other end.

Figure 2:
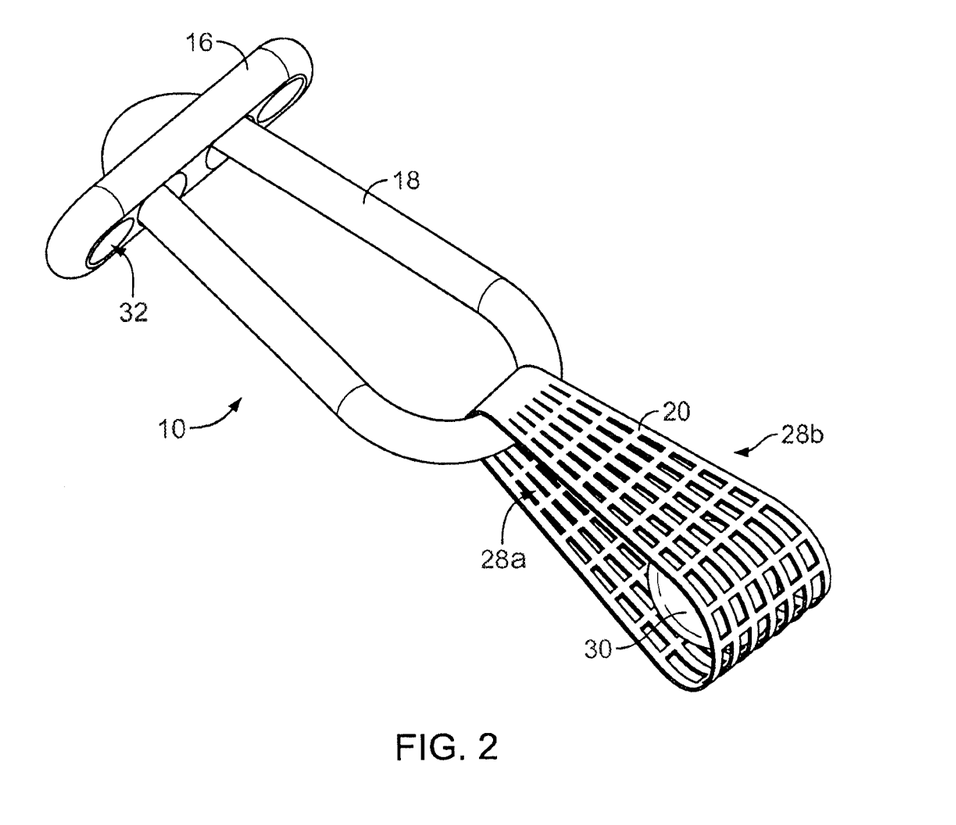
FIG. 2 is a perspective view of the graft attachment device.

Referring also to FIG. 2, the enclosure member 20 of the graft attachment device 10 is generally a sac-like structure that can be made from a braided or woven mesh of suture material, such as #5 Ultrabraid suture, a natural material, such as collagen, or a combination thereof. The enclosure member 20 has two openings 28a, 28b positioned on opposite portions of the enclosure member 20. The openings 28a, 28b can allow the enclosure member 20 to receive and hold a biologic material 30 as discussed further below. Alternatively, the enclosure member can have a single opening, more than two openings, or no openings. A plurality of filaments, threads, sutures, or the like can be attached to portions of the enclosure member 20 to help, for example, couple the enclosure member 20 to other parts of the graft attachment device 10 or the tissue graft 22. In some cases, the enclosure member 20 can be a continuous band of suture material. Alternatively, the enclosure member 20 can be a scaffold-like structure configured to be impregnated with the biologic material 30.

The graft connecting element 18 of the graft attachment device 10 couples the tissue graft 22 (FIGS. 1A-1B) to the graft attachment device 10 as discussed further below. As shown in FIG. 2, the graft connecting element 18 can be a continuous loop of suture, such as #5 Ultrabraid suture, or other material, such as polyester, that is looped through openings 28a, 28b of the enclosure member 20 and openings 32 of the platform member 16 to couple the enclosure member 20 to the platform member 16. Alternatively, or additionally, the graft connecting element 18 can be coupled to the enclosure member 20 and the platform member 16 via various filaments and other attachment elements (not shown).

The platform member 16 of the graft attachment device 10 can be positioned on a cortical surface of the femur 14 (FIGS. 1A-1B) and helps secure the graft attachment device 10 and the tissue graft 22 within the femoral tunnel 12a, 12b. Various sutures can be looped through one or more openings 32 of the platform member 16 and used by a surgeon to pull the platform member 16 through the femoral tunnel 12a, 12b and position the platform member 16 on the cortical surface of the femur 14 as desired.

In addition to various filaments, threads, sutures, or the like, the graft attachment device 10 can include components formed from any biocompatible material or a combination of biocompatible materials, such as certain metal alloys and polymers. Components of the graft attachment device 10 can include non-absorbable materials such as PEEK or Acetal. Alternatively, or additionally, components of the graft attachment device 10 can include bioabsorbable materials such as PLLA.

During surgery, a surgeon inserts the biologic material 30 into the enclosure member 20 via the opening 28a, 28b prior to attachment of the tissue graft 22. The biologic material 30 can be a fibrin clot or any other material that facilitates ligament or tissue repair. For example, the biologic material 30 can include any biocompatible material or a combination of biocompatible materials such as, but not limited to, platelet rich plasma (PRP), hyaluronic acid (HA), growth factors (e.g. PDGF, FGF, BMP, GDF-5, and other members of the TGF-$\beta$ superfamily), autologous tissue fragments, and pharmacologic agents (e.g. anti-inflammatory and/or analgesic). Alternatively, or additionally, the biologic material 30 can be pressed into a surface of the enclosure member 20 such that the biologic material 30 is formed around the surface. The enclosure member 20 can be pre-attached to the graft attachment device 10 during manufacture. Alternatively, the enclosure member 20 can be coupled to the graft attachment device 10 prior to or following insertion of the biologic material 30 into the enclosure member 20. In some cases, the surgeon can close the openings 28a, 28b, for example using sutures, to prevent the biologic material 30 from coming out of the enclosure member 20.

The biologic material 30 can help promote healing following surgery, such as ACL reconstruction. For example, the fibrin clot, a paste-like material typically prepared from a patient's blood, can enhance healing between graft bundles as well as between the graft bundles and bone by releasing various growth factors and chemical substances that promote healing.

Figures 3A, 3B:
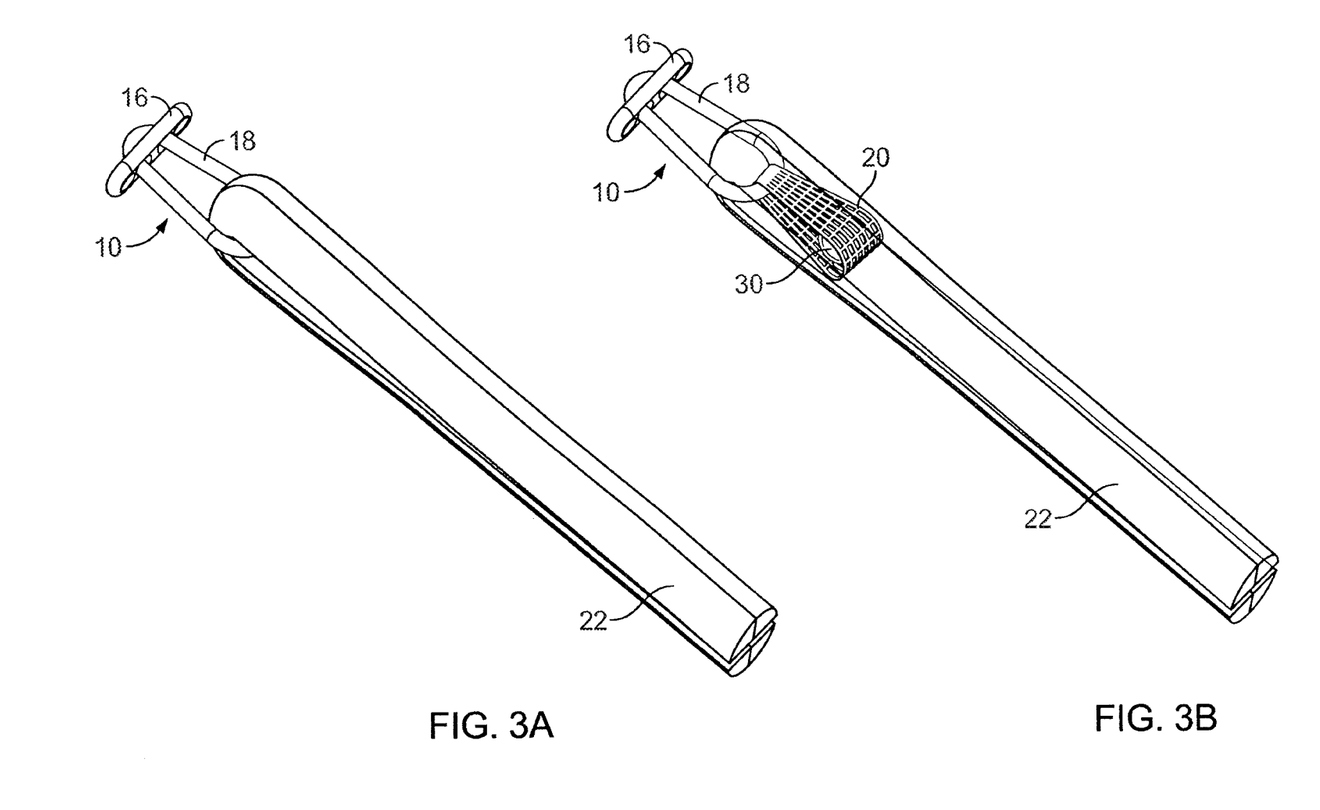
FIGS. 3A-3B are perspective views of the graft attachment device coupled to a tissue graft.

Referring to FIGS. 3A and 3B, following insertion of the biologic material 30 into the enclosure member 20, the surgeon can attach the tissue graft 22, which can comprise semitendinosus and gracilis grafts or two halves of a semitendinosus graft, to the graft attachment device 10 by passing the graft 22 through the graft connecting element 18 and doubling over to produce, for example, a quadrupled bundle. During the attachment process, the tissue graft 22 can be folded over the enclosure member 20 such that the biologic material 30 contained within the enclosure member 20 comes in contact with an inner surface of the folded-over tissue graft 22. In some cases, the enclosure member 20 can be positioned proximate an outer surface of the folded-over tissue graft 22.

Figure 4:
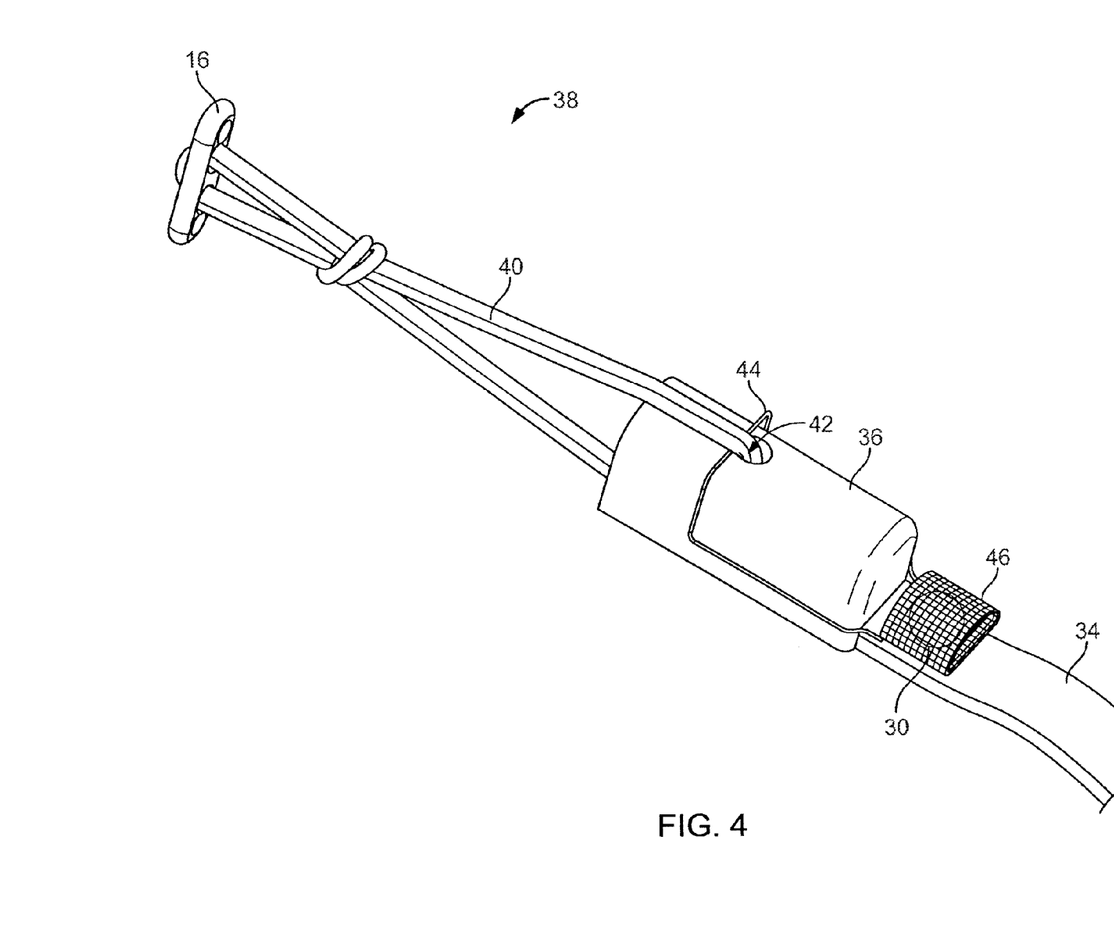
FIG. 4 is a perspective view of an alternative graft attachment device coupled to an alternative tissue graft.

Referring to FIG. 4, in some cases a tissue graft 34 having a bone block 36 can be attached to a graft attachment device 38. The bone block 36 is generally shaped and sized in close conformity with the femoral tunnel 12a, 12b to promote optimal healing. The tissue graft 34, for example a patellar tendon graft, can be attached to the graft attachment device 38 by looping a graft connection element 40 through an opening 42 in the bone block 36. During this process, the graft attachment device 38 can also be looped through an attachment portion 44 of a enclosure member 46. The biologic material 30 can be inserted into the enclosure member 46 as described above. Following attachment of the tissue graft 34 and the enclosure member 46 to the graft attachment device 38, the enclosure member 46 is generally positioned below the bone block 36 and proximate a ligament portion of the tissue graft 34.

Prior to implanting the graft attachment devices 10, 38 and the respectively attached tissue grafts 22, 34, the femoral tunnel 12a, 12b can be drilled from an intercondylar notch of the femur 14 towards the cortical surface of the femur 14. The tibial tunnel 24 can be drilled from an anterior region of the tibia 26 towards the intercondylar notch.

During implantation, the graft attachment device 10, 38, and the attached tissue graft 22, 34, respectively, can be positioned within the femoral tunnel 12a, 12b using lead sutures (not shown) that can be looped through one or more openings 32 of the platform member 16. For example, the lead sutures are passed through the femoral tunnel 12a, 12b from an opening near the intercondylar notch and used to pull the graft attachment device 10, 38 through the femoral tunnel 12a, 12b and towards an opening near the cortical surface of the femur 14. After the platform member 16 exits the femoral tunnel 12a, 12b through the opening near the cortical surface, the lead sutures can be used to flip and position the platform member 16 so that the member 16 lies flat against the cortical surface of the femur 14 and at least a portion of the tissue graft 22, 34 is positioned within the femoral tunnel 12a, 12b. A distal end of the attached tissue graft 22, 34 can extend out of the opening near the intercondylar notch.

In addition to promoting healing at a ligament injury site, such as following an ACL reconstruction surgery, the biologic material 30 can help enhance healing at a soft tissue injury site, for example in a meniscal tissue repair. In a meniscal tear repair procedure, a fibrin clot or PRP, for example, can be inserted into a meniscal tear to promote healing, especially in meniscal regions of low vascularity such as red-white and white-white regions of a meniscus.

Figure 5:
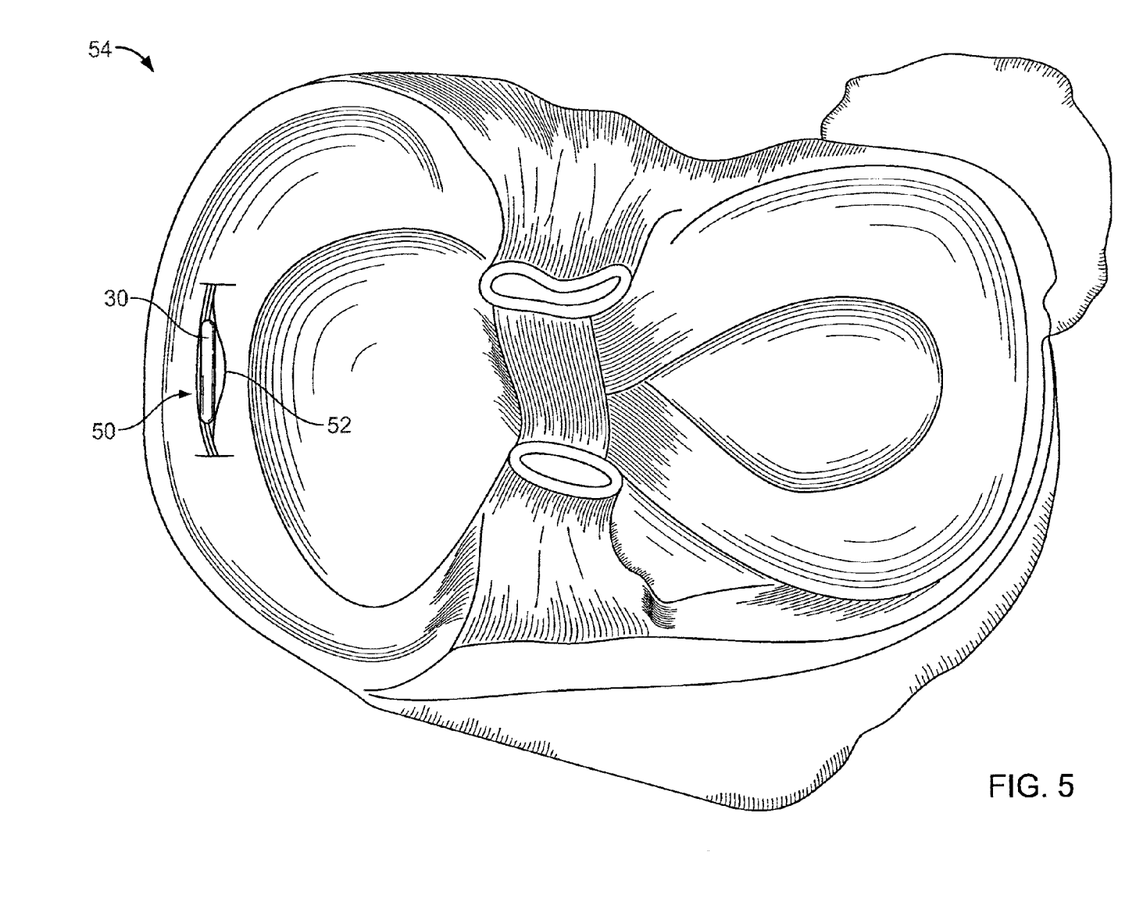
FIG. 5 is a top view of a suture scaffold implanted within a meniscal tear.
Figure 6:
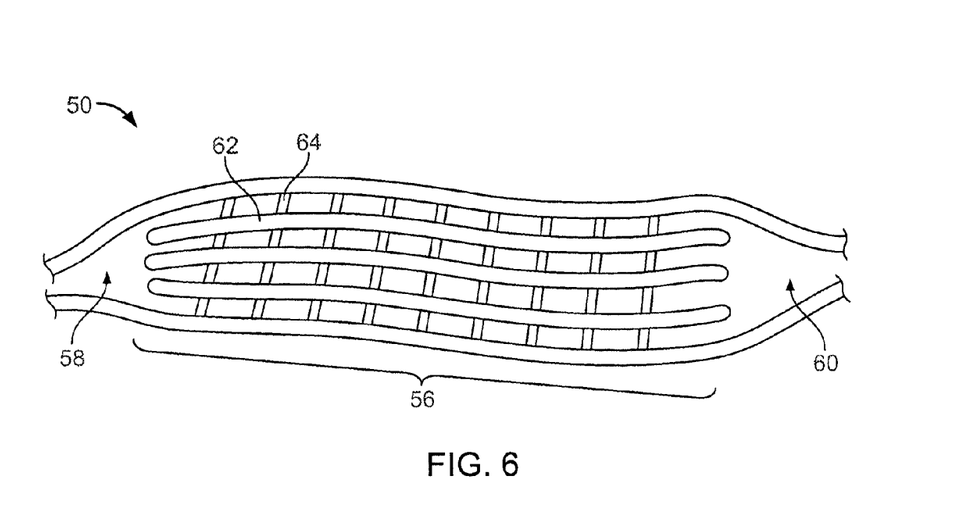
FIG. 6 is a side view of the suture scaffold.

Referring to FIGS. 5 and 6, a suture scaffold 50 is designed to hold the biologic material 30 and can be inserted into a tear 52 in a meniscus 54 to promote healing. The suture scaffold 50 includes a central portion 56 and one or more guide portions 58, 60 proximately attached to a border or edge region of the central portion 56.

The central portion 56 of the suture scaffold 50 is configured to be impregnated with the biologic material 30 so that the biologic material 30 may be readily delivered and secured to the soft tissue injury site during surgery. For example, the central portion 56 can include a plurality of horizontally oriented sutures 62 and transversely oriented sutures 64 that are woven together to form a mesh surface. The horizontal and transverse sutures 62, 64 of the central portion 56 can be arranged such that the resulting mesh is sufficiently sparse to allow a biologic material to be pushed at least partially through its surface, yet dense enough to hold the pushed-through biologic material in place. In some implementations, the sutures 62, 64 can have a rough surface texture, or other surface properties, that aids in holding the pushed-through biologic material in place. In use, the surgeon can impregnate the central portion 56 with the biologic material 30, for example a fibrin clot, by pressing the biologic material 30 into the mesh surface of the central portion 56. Horizontal sutures 62 and transverse sutures 64 of the central portion 56 hold the biologic material 30 within the central portion 56 and can impart increased structural integrity to the biologic material 30 to aid in handling and delivery of the material 30. Alternatively, or additionally, the biologic material 30 can be chemically formed around the central portion 56, for example through coagulation of fibrinogen by thrombin.

As shown in FIG. 6, one or more guide portions 58, 60 of the suture scaffold 50 are attached to an edge region of the central portion 56 and can help position the central portion 56 and the impregnated biologic material 30 at a desired location within the tear 52 (FIG. 5). For example, the guide portions 58, 60 can include one or more horizontal sutures 62 extending out from opposing ends of the woven mesh surface of the central portion 56. Alternatively, or additionally, the guide portions 58, 60 can include one or more transverse sutures 64 extending out from opposing ends of the woven mesh surface of the central portion 56. In some cases, the guide portions 58, 60 can be absorbable or non-absorbable structures that are separately attached to one or more edge regions of the central portion 56.

Figure 7A:
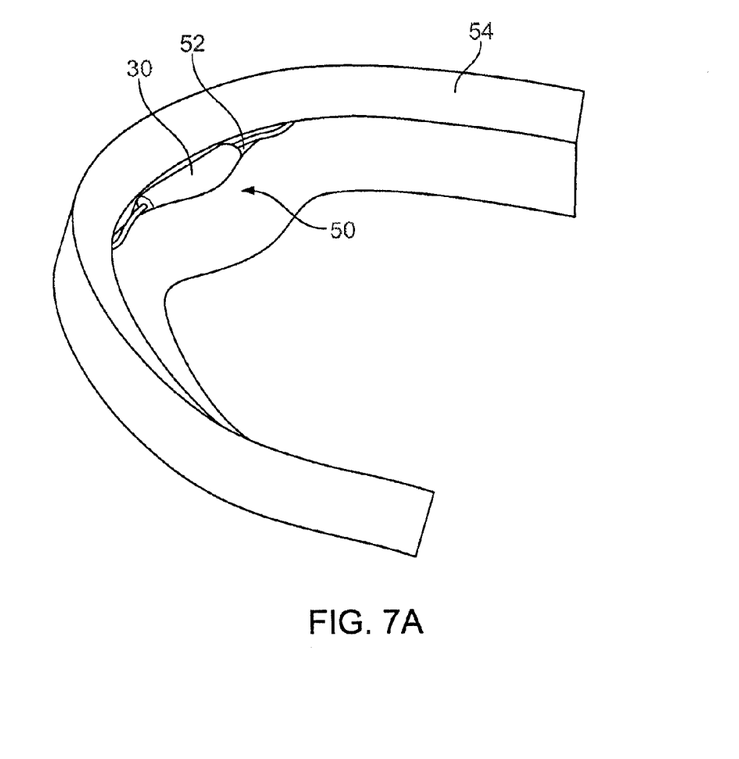
FIG. 7A is a perspective view of the suture scaffold implanted within the meniscal tear.
Figure 7B:
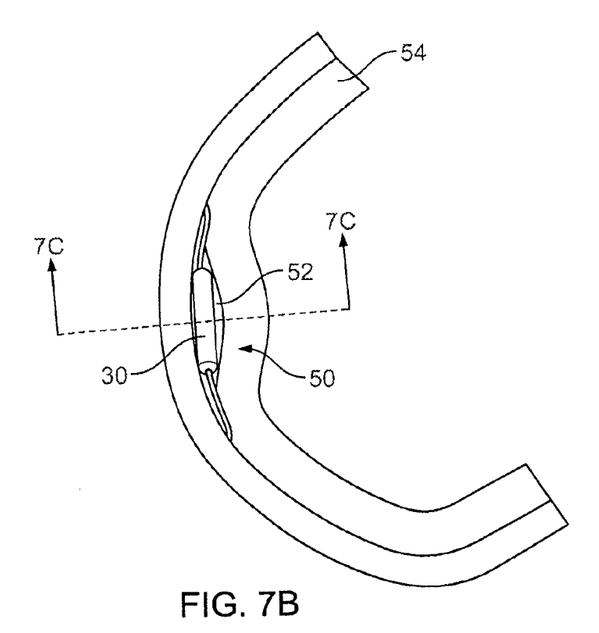
FIG. 7B is another top view of the suture scaffold implanted within the meniscal tear.
Figure 7C:
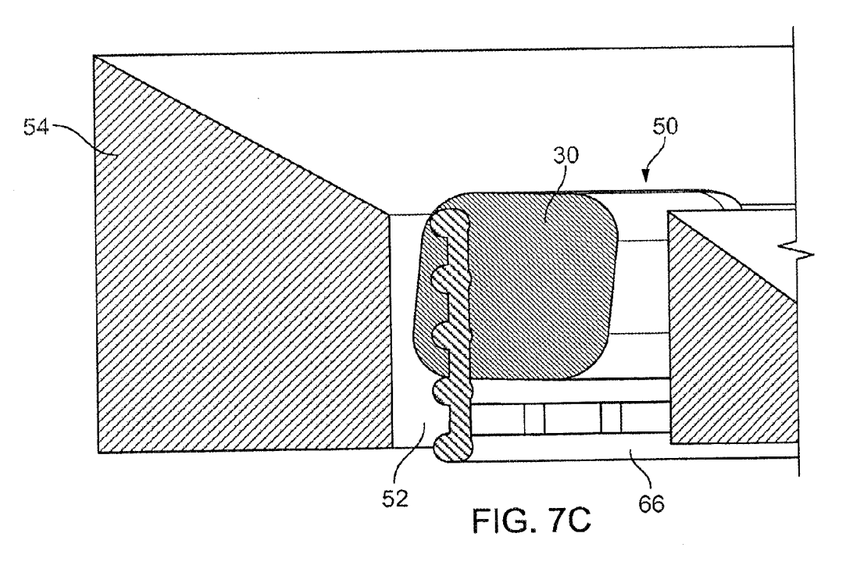
FIG. 7C is a cross-sectional perspective view of the suture scaffold of FIG. 7B taken along the line 7C-7C.

During a meniscal tear repair procedure, as shown in FIGS. 7A-7C, the surgeon can implant the suture scaffold 50 and the impregnated biologic material 30 into the tear 52. For example, the surgeon can guide a leading edge 66 (FIG. 7C) of the suture scaffold 50 into the tear 52 until the suture scaffold 50 and the biologic material 30 are generally positioned at an appropriate depth within the tear 52. Then, the surgeon can move the central portion 56 and the impregnated biologic material 30 to a final desired position within the tear 52 by pulling, pushing, and otherwise manipulating the guide portions 58, 60 until the desired positioning of the biologic material 30 is obtained. After the desired positioning of the biologic material 30 is obtained, the guide portions 58, 60 can be removed, for example by cutting, or left in place. In some cases, the entire suture scaffold 50 can be removed, leaving only the biologic material 30 in place within the meniscal tear 52. Implantation of the biologic material 30 into the meniscal tear 52 can be used with other meniscal tear repair procedures and tools to enhance healing at the repair site.

While this document contains many specific implementation details, these should not be construed as limitations on the scope of any implementations or of what may be claimed, but rather as descriptions of features specific to particular implementations of particular implementations. Certain features that are described in this document in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Thus, particular implementations of the subject matter have been described. Other implementations are within the scope of the following claims.

What is claimed is:
1. A method of repairing soft tissue tear, comprising:
providing a scaffold comprising a central portion comprising filaments arranged in a weave pattern, said central portion impregnated with a biologic material, the scaffold further comprising a guide portion having one or more filaments continuously extending out from the weave pattern of the central portion;

inserting an edge of the scaffold into the soft tissue tear; and guiding the edge of the scaffold with the guide portion until the biologic material in the central portion of the scaffold is positioned at a depth within the soft tissue tear, wherein the manipulation of the guide portion comprises removing the guide portion after the biological material is implanted in the tear, wherein the biological material helps promote repairing of the soft tissue tear.

2. The method of claim 1, wherein the impregnation of the central portion of the scaffold with the biologic material comprises forming at least one of a fibrin clot or a platelet rich plasma around the central portion.

3. The method of claim 1, wherein the impregnation of the central portion of the scaffold comprises pressing into the central portion at least one of a fibrin clot or a platelet rich plasma.

4. The method of claim 3, wherein the fibrin clot or the platelet rich plasma fibrin clot release growth factors and chemical substances that promote the soft tissue repair.

5. The method of claim 1, wherein the scaffold is implanted into the soft tissue tear.

6. The method of claim 1, wherein the biologic material promotes healing of the soft tissue.

7. The method of claim 1, wherein the soft tissue is a meniscus.

8. The method of claim 7, wherein the meniscus comprises meniscal regions of low vascularity comprising red-white and white-white regions of the meniscus.

9. The method of claim 1, wherein the manipulation of the guide portion comprises pulling the guide portion such that the biological material comes in contact with the soft tissue.

10. The method of claim 1, wherein the manipulation of the guide portion comprises pushing the guide portion such that the biological material comes in contact with the soft tissue.

11. The method of claim 1, wherein the guide portion comprises a first guide portion attached to a first edge of the central portion, and a second guide portion attached to a second edge of the central portion, the second edge being opposite the first edge.

12. The method of claim 1, wherein the central portion comprises a plurality of horizontally oriented sutures and transversely oriented sutures that are woven together to form a mesh surface.

13. The method of claim 12, wherein the horizontal sutures and transverse sutures of the central portion hold the biologic material.

14. The method of claim 1, wherein the impregnation of the biological material to the central portion optionally comprises chemically bonding the biological material around the central portion.

15. The method of claim 14, wherein the chemical bonding is through a coagulation of the biological material around the central portion.

16. The method of claim 1, wherein the biologic material comprises a biocompatible material or a combination of biocompatible materials.

17. The method of claim 16, wherein the biocompatible material is selected from the group consisting of platelet rich plasma (PRP), hyaluronic acid (HA), growth factors, autologous tissue fragments, pharmacologic agents and a combination thereof.

18. The method of claim 17, wherein the growth factor is selected from the group consisting of PDGF, FGF, BMP, GDF-5, members of the TGF-beta superfamily, and a combination thereof.

19. The method of claim 17, wherein the pharmacologic agent is selected from the group consisting of anti-inflammatory agents, analgesic agents, and a combination thereof.

* * * * *